(12) United States Patent  (10) Patent No.: US 9,198,762 B2
Collazo  (45) Date of Patent: Dec. 1, 2015

(54) BICRUCIATE RETAINING TIBIAL BASEPLATE

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

(*) Notice: Subject to any disclaimer, the term of this patent is extended or adjusted under 35 U.S.C. 154(b) by 0 days.

(21) Appl. No.: 14/176,401

(22) Filed: Feb. 10, 2014

(65) Prior Publication Data

US 2014/0156016 A1  Jun. 5, 2014

Related U.S. Application Data

(62) Division of application No. 12/987,380, filed on Jan. 10, 2011, now Pat. No. 8,728,167.

(51) Int. Cl.
*A61F 2/38* (2006.01)
*A61B 17/15* (2006.01)
(Continued)

(52) U.S. Cl.
CPC .............. *A61F 2/389* (2013.01); *A61B 17/157* (2013.01); *A61B 17/1604* (2013.01); *A61F 2002/30131* (2013.01); *A61F 2002/30688* (2013.01); *A61F 2002/30892* (2013.01)

(58) Field of Classification Search
CPC ....... A61F 2/38; A61F 2/3854; A61F 2/3868; A61F 2/3886; A61F 2/389
USPC ..................... 623/20.14–20.17, 20.21–20.29, 623/20.31–20.34, 14.12
See application file for complete search history.

(56) References Cited

U.S. PATENT DOCUMENTS 3,798,679 A  3/1974  Ewald
3,816,855 A  6/1974  Saleh
(Continued)

FOREIGN PATENT DOCUMENTS

EP  0306744 A2  3/1989
EP  1011542 A1  6/2000
(Continued)

OTHER PUBLICATIONS

Pritchett, James W., BioPro: Equalizer Modular Total Knee Replacement, available at least as early as 1999, 19 pages.
(Continued)

*Primary Examiner* — Marcia Watkins
(74) *Attorney, Agent, or Firm* — Lerner, David, Littenberg, Krumholz & Mentlik, LLP

(57) ABSTRACT

A base component for a tibial implant has a lateral compartment and a medial compartment spaced from the lateral compartment defining an open central section therebetween. A connecting portion connects the medial and lateral compartments at an anterior end of the base component which anterior end is located adjacent the anterior tibia. The open central section of the base component intermediate the spaced medial and lateral compartments is open to a posterior end of the base component. The medial and lateral compartments have a bone contacting surface and a superiorly facing surface. The connecting portion has a curved anteriorly facing surface and has a first angled surface extending at an angle from adjacent the anterior end of the base component at a bone contacting surface of the connecting portion superiorly to a posterior end of the connecting portion. The first angled surface defining an anterior end of the open central section.

17 Claims, 16 Drawing Sheets

(51) Int. Cl.
*A61B 17/16* (2006.01)
*A61F 2/30* (2006.01)

(56) References Cited

U.S. PATENT DOCUMENTS

| | | |
|---|---|---|
| 3,869,731 A | 3/1975 | Waugh et al. |
| 4,207,627 A | 6/1980 | Cloutier |
| 4,586,933 A | 5/1986 | Shoji et al. |
| 4,711,639 A | 12/1987 | Grundei |
| 4,769,040 A | 9/1988 | Wevers |
| 4,822,362 A | 4/1989 | Walker et al. |
| 5,037,439 A | 8/1991 | Albrektsson et al. |
| 5,137,536 A | 8/1992 | Koshino |
| 5,171,283 A | 12/1992 | Pappas et al. |
| 5,282,868 A | 2/1994 | Bahler |
| 5,509,934 A | 4/1996 | Cohen |
| 5,658,341 A | 8/1997 | Delfosse |
| 5,702,464 A | 12/1997 | Lackey et al. |
| 5,755,801 A | 5/1998 | Walker et al. |
| 5,824,103 A | 10/1998 | Williams |
| 5,879,394 A | 3/1999 | Ashby et al. |
| 6,258,127 B1 | 7/2001 | Schmotzer |
| 6,387,131 B1 | 5/2002 | Miehlke et al. |
| 6,436,145 B1 | 8/2002 | Miller |
| 6,482,209 B1 | 11/2002 | Engh et al. |
| 6,558,421 B1 | 5/2003 | Fell et al. |
| 6,652,588 B2 | 11/2003 | Hayes, Jr. et al. |
| 6,679,914 B1 | 1/2004 | Gabbay |
| 6,699,291 B1 | 3/2004 | Augoyard et al. |
| 6,896,702 B2 | 5/2005 | Collazo |
| 6,969,393 B2 | 11/2005 | Pinczewski et al. |
| 7,060,101 B2 | 6/2006 | O'Connor et al. |
| 7,066,963 B2 | 6/2006 | Naegerl |
| 7,115,131 B2 | 10/2006 | Engh et al. |
| 7,261,740 B2 | 8/2007 | Tuttle et al. |
| 7,294,149 B2 | 11/2007 | Hozack et al. |
| 7,458,933 B2 | 12/2008 | LeVahn et al. |
| 7,462,199 B2 | 12/2008 | Justin et al. |
| 7,578,850 B2 | 8/2009 | Kuczynski et al. |
| 7,625,407 B2 | 12/2009 | Akizuki et al. |
| 7,635,390 B1 | 12/2009 | Bonutti |
| 7,695,519 B2 | 4/2010 | Collazo |
| 7,758,652 B2 | 7/2010 | Engh et al. |
| 7,766,969 B2 | 8/2010 | Justin et al. |
| 7,771,483 B2 | 8/2010 | Justin et al. |
| 7,771,484 B2 | 8/2010 | Campbell |
| 7,799,086 B2 | 9/2010 | Justin et al. |
| 7,828,852 B2 | 11/2010 | Bonutti |
| 8,066,776 B2 | 11/2011 | O'Connor et al. |
| 8,092,546 B2 | 1/2012 | Coon et al. |
| 8,105,387 B2 | 1/2012 | Barnett et al. |
| 8,114,165 B2 | 2/2012 | Rhodes et al. |
| 8,128,703 B2 | 3/2012 | Hazebrouck et al. |
| 8,137,407 B2 | 3/2012 | Todd et al. |
| 8,157,869 B2 | 4/2012 | Metzger et al. |
| 8,211,181 B2 | 7/2012 | Walker |
| 8,292,964 B2 | 10/2012 | Walker |
| 8,292,965 B2 | 10/2012 | Walker |
| 8,343,227 B2 | 1/2013 | Metzger et al. |
| 8,403,994 B2 | 3/2013 | Maloney et al. |
| 8,500,818 B2 | 8/2013 | Metzger et al. |
| 8,529,631 B2 | 9/2013 | Donno et al. |
| 8,568,486 B2 | 10/2013 | Wentorf et al. |
| 8,574,304 B2 | 11/2013 | Wentorf et al. |
| 8,603,101 B2 | 12/2013 | Claypool et al. |
| 8,613,775 B2 | 12/2013 | Wentorf et al. |
| 2004/0030397 A1 | 2/2004 | Collazo |
| 2004/0138755 A1 | 7/2004 | O'Connor et al. |
| 2005/0154472 A1* | 7/2005 | Afriat ................... 623/20.29 |
| 2005/0283251 A1 | 12/2005 | Coon et al. |
| 2006/0004460 A1 | 1/2006 | Engh et al. |
| 2006/0195196 A1 | 8/2006 | Pendleton et al. |
| 2006/0212124 A1 | 9/2006 | Siebel |
| 2006/0265079 A1 | 11/2006 | D'Alessio |
| 2007/0010890 A1 | 1/2007 | Collazo |
| 2007/0203582 A1 | 8/2007 | Campbell |
| 2008/0119941 A1 | 5/2008 | Seo et al. |
| 2009/0187251 A1 | 7/2009 | Justin et al. |
| 2009/0270995 A1 | 10/2009 | Rhodes et al. |
| 2009/0319048 A1 | 12/2009 | Shah et al. |
| 2009/0326663 A1* | 12/2009 | Dun ........................ 623/20.21 |
| 2010/0016980 A1 | 1/2010 | Donno et al. |
| 2010/0280624 A1 | 11/2010 | Engh et al. |
| 2010/0305575 A1 | 12/2010 | Wilkinson et al. |
| 2010/0305710 A1 | 12/2010 | Metzger et al. |
| 2010/0305711 A1 | 12/2010 | McKinnon et al. |
| 2010/0331847 A1 | 12/2010 | Wilkinson et al. |
| 2010/0331848 A1 | 12/2010 | Smith et al. |
| 2010/0331991 A1 | 12/2010 | Wilkinson et al. |
| 2011/0015749 A1 | 1/2011 | Engh et al. |
| 2011/0066248 A1 | 3/2011 | Ries et al. |
| 2011/0066249 A1 | 3/2011 | Justin et al. |
| 2011/0082559 A1 | 4/2011 | Hartdegen et al. |
| 2011/0098824 A1 | 4/2011 | Jukes et al. |
| 2011/0190898 A1 | 8/2011 | Lenz et al. |
| 2011/0264097 A1 | 10/2011 | Hodorek et al. |
| 2012/0035736 A1 | 2/2012 | O'Connor et al. |
| 2012/0078262 A1 | 3/2012 | Pinczewski et al. |
| 2012/0179266 A1 | 7/2012 | Collazo |
| 2012/0209394 A1 | 8/2012 | Bojarski et al. |
| 2012/0316563 A1 | 12/2012 | Metzger et al. |
| 2012/0330429 A1 | 12/2012 | Axelson, Jr. et al. |
| 2013/0006375 A1 | 1/2013 | Metzger et al. |
| 2013/0024001 A1 | 1/2013 | Wentorf et al. |
| 2013/0046385 A1 | 2/2013 | Hartdegen et al. |
| 2013/0131817 A1 | 5/2013 | Parisi et al. |
| 2013/0131819 A1 | 5/2013 | Parisi et al. |
| 2013/0173010 A1 | 7/2013 | Irwin et al. |
| 2013/0204383 A1 | 8/2013 | Wentorf |
| 2013/0245777 A1 | 9/2013 | Jerry |
| 2013/0289731 A1 | 10/2013 | Katerberg et al. |
| 2013/0345820 A1 | 12/2013 | Maloney et al. |
| 2014/0025175 A1 | 1/2014 | Wentorf et al. |
| 2014/0025176 A1 | 1/2014 | Wentorf et al. |
| 2014/0025177 A1 | 1/2014 | Wentorf et al. |
| 2014/0067076 A1 | 3/2014 | Collazo |

FOREIGN PATENT DOCUMENTS

| | | |
|---|---|---|
| FR | 2676916 A1 | 12/1992 |
| WO | 9858603 A1 | 12/1998 |
| WO | 0076428 A1 | 12/2000 |
| WO | 2006012370 A2 | 2/2006 |
| WO | 2009158318 A1 | 12/2009 |
| WO | WO 2009158318 A1 * | 12/2009 |
| WO | 2010006677 A1 | 1/2010 |
| WO | 2010138836 A2 | 12/2010 |
| WO | 2010138841 A2 | 12/2010 |
| WO | 2010138850 A2 | 12/2010 |
| WO | 2010138854 A2 | 12/2010 |
| WO | 2010138857 A2 | 12/2010 |
| WO | 2011094540 A2 | 8/2011 |
| WO | 2012178031 | 12/2012 |
| WO | 2013101582 | 7/2013 |
| WO | 2013148954 | 10/2013 |

OTHER PUBLICATIONS

Townley, Charles O., Total Knee Arthroplasty: A Personal Retrospective and Prospective Review, Clinical Orthopaedics and Related Research, No. 236, 1988, 15 pages.

BioPro, Equalizer Modular Total Knee Replacement, date not known.

Freeman-Swanson Total Knee Prosthesis, Vitallium Alloy Femoarl Component, 1978.

Howmedica, Inc. Cruciate-Condylar Total Knee Surgical Technique, 1979.

Howmedica, Inc. The Howmedica Kinematic Knee System, 1980.

International Search Report and Written Opinion, PCT/US2012/0020719, dated Mar. 19, 2012.

Townley Total Knee Prosthesis, Vitallium Alloy Femoral Component, 1978.

(56) References Cited

OTHER PUBLICATIONS

International Search Report and Written Opinion for Application No. PCT/US2014/017664 dated Jun. 6, 2014.
International Search Report and Written Opinion for International Application No. PCT/US2012/070531, mailed May 27, 2013, 17 pages.
Partial International Search Report for Application No. PCT/US2014/017664 dated Apr. 16, 2014.
Townley, Charles O., Total Knee Arthroplasty: A Personal Retrospecteive and Prospective Review, Clinical Orthopaedics and Related Research, No. 236, 1988, 15 pages.

* cited by examiner

BICRUCIATE RETAINING TIBIAL BASEPLATE

CROSS-REFERENCE TO RELATED APPLICATIONS

This application is a divisional of U.S. application Ser. No. 12/987,380 filed Jan. 10, 2011, which is now U.S. Pat. No. 8,728,167, the disclosures of which are incorporated herein by reference.

BACKGROUND OF THE INVENTION

Bicruciate retaining baseplates are known and have been in use since at least the early 1970s. Their use allows the preservation of both cruciate ligaments, the anterior cruciate ligament (ACL) and the posterior cruciate ligament (PCL). Early designs were predominantly bicompartmental, i.e., the articular cartilage of the distal femur and the proximal tibia was replaced to alleviate pain and restore function, but not the patella and corresponding trochlear groove. However, starting in the late 1970s, the use of bicruciate retaining baseplates started to decline as the introduction of the tricompartmental knees gained popularity and are not generally used in the current day knee joint replacement.

There is a never ending quest to improve/restore natural knee kinematics following total knee replacement especially with the baby boomer generation getting surgery at a much younger age and still expecting a return to normal, active lifestyle activities such as golf, biking, hiking, and skiing. However, modern day implants still have limitations in offering natural joint kinematics. For example, a common misnomer in what the surgical community presently refers to as a Cruciate Retaining (CR) knee, the PCL is preserved but not the ACL. Therefore, the best that this knee can ever be is equivalent to an ACL deficient knee. In a Posterior Stabilized (PS) knee, both cruciates are sacrificed and only a partial function of the PCL is restored through the use of a cam on the femoral component and a post on the tibial insert, well known and understood in the current art. Therefore, since knees with compromised or torn cruciates are intrinsically unstable, it is believed that preserving both cruciates would improve joint stability and function following Total Knee Arthroplasty.

Some drawbacks of prior art bicruciate retaining baseplate designs are avulsion (tearing away) of the tibial eminence, and less than optimal instrumentation making surgery more challenging. In all bicruciate retaining baseplates, the medial and lateral compartments are connected by an anterior bridge portion. The corresponding bone preparation for the bridged portion is made with a vertical cut anterior to the ACL insertion site and extends distally to intersect the resection plane thereby resulting in a 90° corner. In loaded conditions, the ACL is under increased tension thereby loading that corner and making it susceptible to avulsion of the eminence. This risk increases significantly if the corner is undercut during preparation thus creating a notch.

BRIEF SUMMARY OF THE INVENTION

The present invention is intended to reduce the risk of avulsing the eminence. The distal surface of the bridged portion of the baseplate is angled. Correspondingly, the bone is prepared by making an angled cut that initiates on the anterior margin of the cortex and extends in a proximal-posterior direction finally exiting on the proximal surface of the eminence, just anterior to the ACL footprint. This angled cut eliminates stress risers especially prevalent in a loaded internal square corner and distributes stress more uniformly across the surface. Another benefit of the present invention is a second angle cut on the anterior-lateral corner of the eminence. The removal of bone in this area provides increased clearance for the saw blade during the transverse cut of the lateral plateau. Tibia preparation, especially the lateral side during cruciate retaining or posterior stabilized procedure is facilitated by subluxing, or displacing the tibia anteriorly to expose the lateral side. The absence of the ACL allows such maneuver. However, with an intact ACL, the joint is much tighter and subluxing the tibia is very limited.

A base component is provided for a tibial implant which component includes a lateral and a medial compartment. The medial compartment is spaced from the lateral compartment defining an opening therebetween straddling a central axis of the implant that is generally aligned with a sagittal plane through the center of the tibia. A bridge or connecting portion connects the medial and lateral compartments at an anterior end of the base component. The connecting portion is located adjacent the anterior tibia upon implantation. The open central section of the base component intermediate the spaced medial and lateral compartments is open to a posterior end of the base component as well as open in the proximal-distal direction. The medial and lateral compartments have a bone contacting surface and a superiorly facing surface adapted to receive an ultrahigh molecular polyethylene bearing component. The connecting portion has a curved anteriorly facing surface and has a first angled surface extending at an angle from adjacent the anterior end of the base component at the bone contacting surface of the connecting portion superiorly and posteriorly to a posterior end of the connecting portion. The first angled surface defines the anterior end of the open central section.

The anterior portion of the major connecting portion is curved in a sagittal plane as well as the normal transverse plane of the anterior surface of a tibial baseplate. The curve of the anterior facing surface of the connecting portion has a radius of curvature centered in a sagittal plane at a point posterior of the connecting portion.

The first angled surface is angled at about 20°-70° to the medial and lateral compartment bone contacting surfaces. The open central section is defined by parallel medially and laterally facing walls, which walls define the boundary of the medial and lateral compartments with regard to the central open section. The angled surface of the connecting portion extends between these parallel medially and laterally facing walls. The lateral wall may have a second angled surface extending at an angle from an anterior end of the first angled surface at the bone contacting surface laterally to the medially facing wall of the lateral compartment. This medially facing wall defines the boundary between the lateral compartment and the open central section. The bone contacting surface in this area extends from the end of the connecting portion nearest the lateral condylar surface laterally, at a second angle, from the lateral edge of the first angled surface to the medially facing wall of the lateral compartment. The superiorly facing surface of the connecting portion is generally planar and the bone contacting surface of the baseplate is also generally planar in the medial and lateral condylar area. The bridge or connecting portion may also have a small planar bone contacting surface area between the most anterior surface of the baseplate and the start of the angled surface posteriorly thereof.

A method for implanting the baseplate component for a tibial implant includes resecting the medial and lateral compartments of the proximal tibia to form two planar surfaces spaced from the anterior cruciate ligament and the posterior cruciate ligament. This resection leaves the central eminence of the tibia in place and utilizes various protectors to ensure that the oscillating saw making the medial and lateral proximal planar cuts on the tibia do not engage this central eminence. Another cutting guide is provided to allow the cutting of a medial and a lateral surface on the tibial eminence, which surface is perpendicular to the plane of the medial and lateral tibial cuts and engages the medially and laterally extending walls of the tibial baseplate component. An additional cutting guide is provided so that an angled surface can be cut on the eminence from the anterior surface thereof, adjacent the planar medial and lateral cuts, proximally and posteriorly at an angle matching the first angled surface on the posteriorly facing surface of the baseplate connection portion. Thus, when the implant is mounted on the proximal tibia, the eminence has an angled surface for contacting the first angled surface on the connecting portion of the baseplate and a second laterally extending surface for contacting the second angled surface on the tibial baseplate portion.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION

Figure 1:
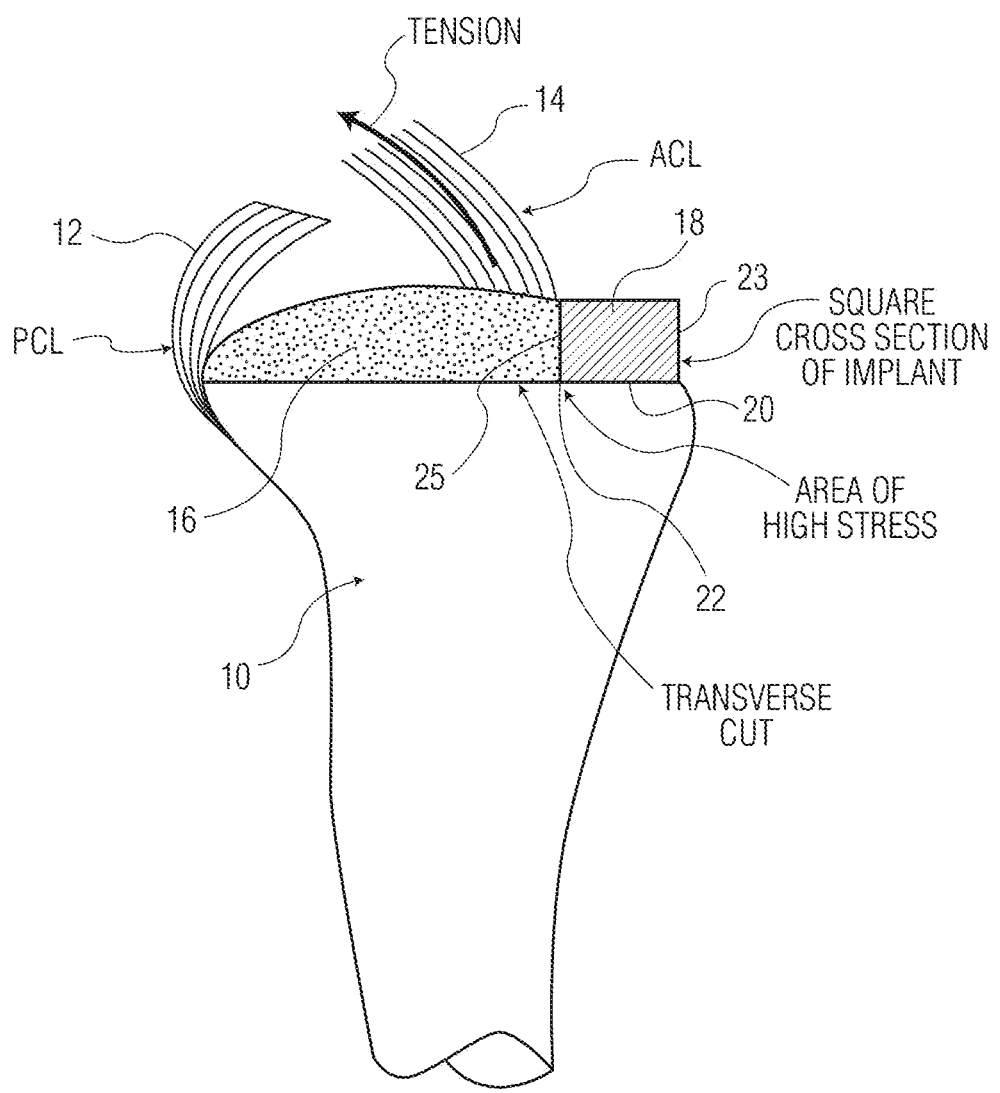
FIG. 1 shows an anterior cross-section along a central sagittal plane of the tibia of a prior art bicruciate retaining tibial baseplate having a rectangular cross-section and a bone contacting surface engaging the proximal resected surface of the tibia.

Referring to FIG. 1, there is shown a proximal tibia 10, including a posterior cruciate ligament 12 and an anterior cruciate ligament 14, including an eminence 16 located about a sagittal plane bisecting the tibia along its anatomic axis. A central cross-section of a prior art bicruciate retaining baseplate 18 is shown having a bone contacting surface 20 and a posterior distal corner 22, which is an area of high stress. This prior art baseplate 18 has planar anterior and posterior surfaces 23 and 25.

Figure 2:
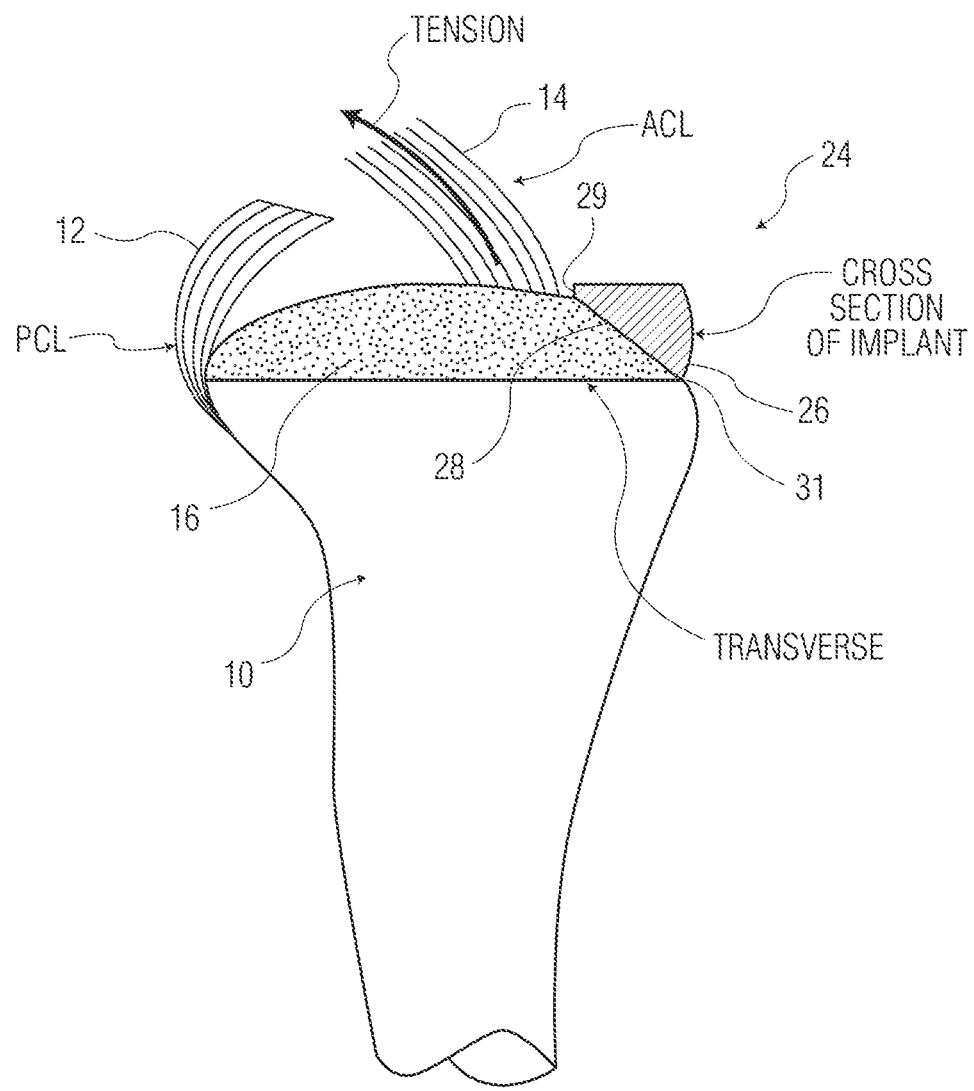
FIG. 2 is a cross-section of the central portion of the bicruciate retaining tibial baseplate of the present invention.

FIG. 2 shows proximal tibia 10, including the posterior cruciate ligament 12 and the anterior cruciate ligament 14 and including eminence 16 and further including, at the anterior surface of eminence 16, the implant of the present invention generally denoted as 24, which is shown in cross-section. The cross-section is taken at a sagittal plane bisecting the medial lateral condyles of the tibia. Implant 24 includes a curved anterior surface 26 and an angled surface 28, which faces generally posterior and inferior. The anterior surface could have a distal flat or straight portion intersecting the curved portion or could be entirely flat.

Figure 3:
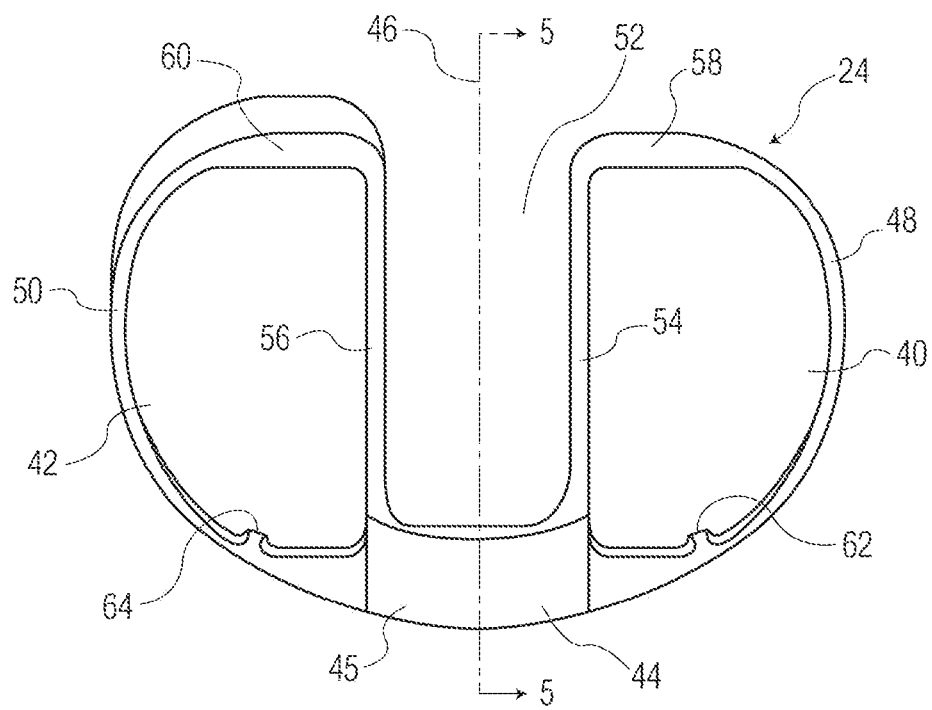
FIG. 3 is a top view of the tibial baseplate of the present invention.

Referring to FIG. 3, there is shown a top view (looking at the superior surface when implanted) of the tibial baseplate or tray 24 of the present invention. Baseplate 24 includes lateral condylar portion 40 and medial condylar portion 42. Portions 40, 42 are designed to receive a typical ultrahigh molecular weight polyethylene (UHMWPE) bearing component (not shown). Medial and lateral condylar portions are connected by a bridge section 44, which, along the sagittal plane defined by axis 46 has a cross-section as shown in FIG. 2. Lateral and medial condylar portions 40, 42 are preferably recessed and surrounded by a raised wall portion 48 laterally and 50 medially to locate the UHMWPE bearing insert. Likewise, U-shaped open area 52 is defined by lateral wall 54 and medial wall 56. Posterior walls 58 and 60 define the posterior ends of recesses 40 and 42, respectively. As is known, undercut grooves may be located adjacent walls 58 and 60 at the superiorly facing surface of condylar portions 40 and 42. This undercut along with tabs 62 and 64 allow the UHMWPE bearing components to be snapped into their respective condylar portions 40, 42.

Figure 4:
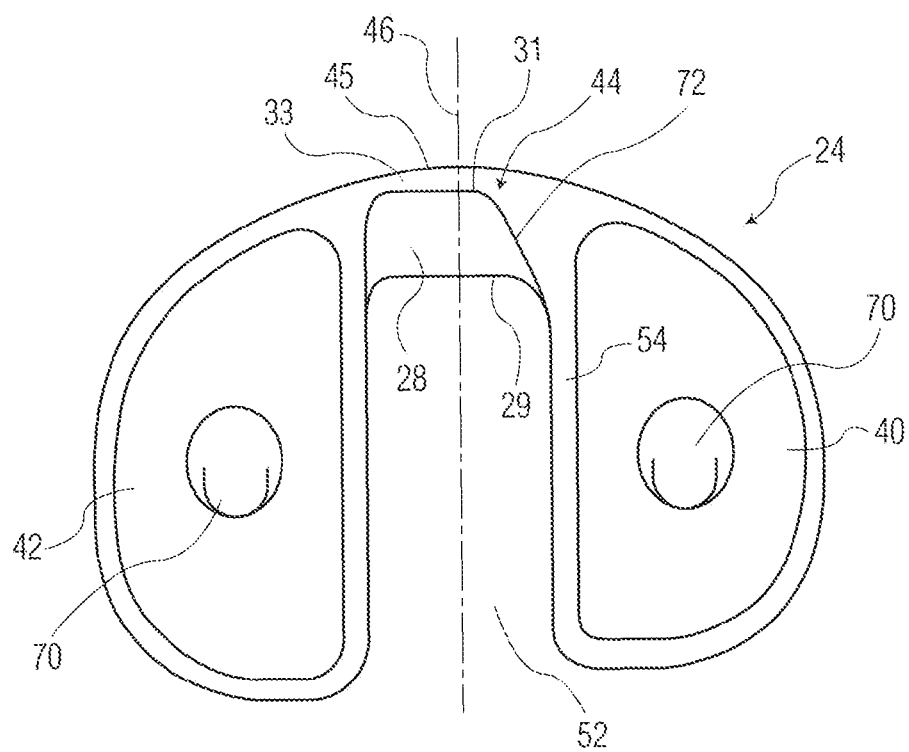
FIG. 4 is a bottom view of the tibial baseplate of the present invention.

Referring to FIG. 4, there is shown a bottom view of tibial baseplate 24 including the bone contacting surface. As seen lateral portion 40 and medial portion 42 are separated by open area 52 and are connected only by bridge portion 44 at the anterior end of the baseplate 45. Angled surface 28 in FIG. 2 is shown extending from adjacent anterior end 45 proximally and posteriorly toward the posterior edge 29 of bridge 44. The anterior-most portion 31 of angled surface 28 is the distal-most contact point with the anterior edge of the eminence 16 of the tibia with posterior edge 29 contacting eminence 16 in a more proximal and posterior position on the eminence. As will be discussed below, the eminence is prepared to receive angled surface 28 of bridge portion 44 in face-to-face contact. Condylar bone contacting surfaces of areas 40, 42 of baseplate 24 may each include a peg 70 and may include a porous coating to encourage bone ingrowth.

The bridge or connector portion 44, at the bone contacting surface, includes a laterally extending edge portion 72, which extends from anterior edge 31 of angled surface 28 to lateral wall 54 of opening 52. In the preferred embodiment, this angled bone contacting surface extends at an angle of 10°-60° with respect to axis 46 in summary.

Figure 5:
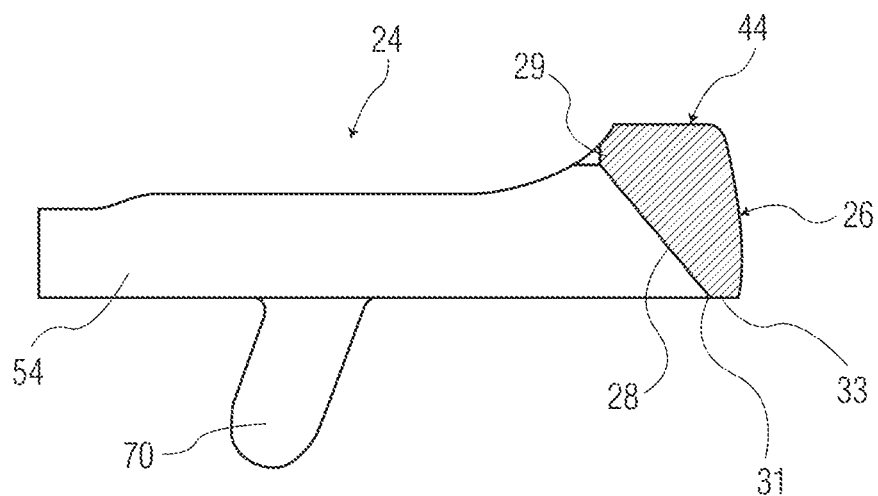
FIG. 5 is a cross-sectional view along lines 5-5 of FIG. 3.

Referring to FIG. 5, there is shown a cross-section view of baseplate 24 along lines 5-5 of FIG. 3. As can be seen, the anterior surface 26 is curved with a radius of approximately one inch center is posterior about one inch. Bone contacting surface 33 extends from the most distal point of anterior surface 26 posteriorly to edge 31, which forms the most anterior and distal point on angled wall 28. Lateral wall 54 defines the lateral edge of opening 52 shown in FIG. 4 and extends posteriorly to end wall 58 as shown in FIG. 3. Pegs 70 of FIGS. 4 and 5 are shown angled posteriorly and are inserted into angled bores in the medial and lateral tibial condylar region generally formed after the proximal tibial cut is made.

Figure 6:
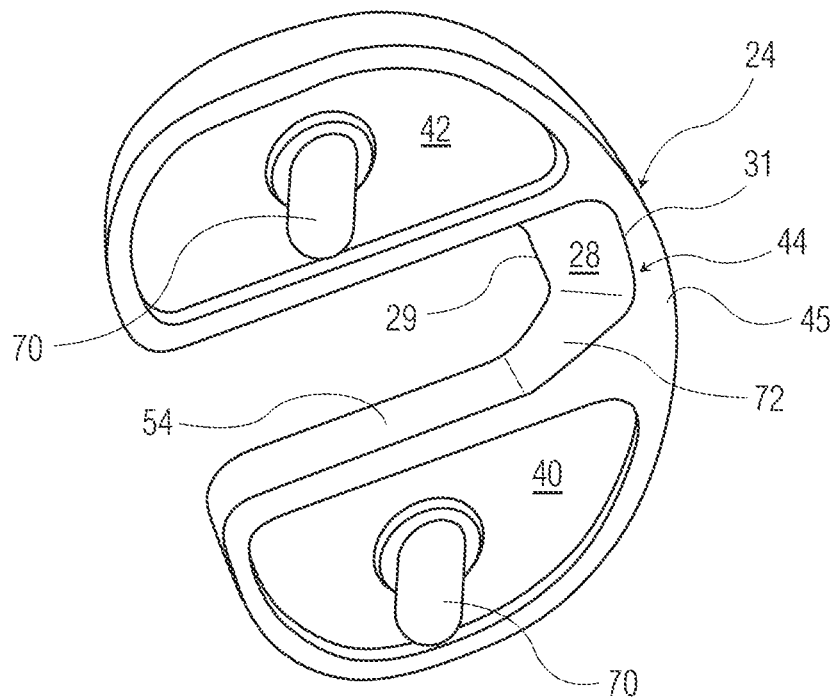
FIG. 6 is an isometric bottom view of the tibial baseplate of FIGS. 3 and 4.

Referring to FIG. 6, there is shown an isometric bottom view of the tibial baseplate 24 shown in FIGS. 3-5.

Figure 7:
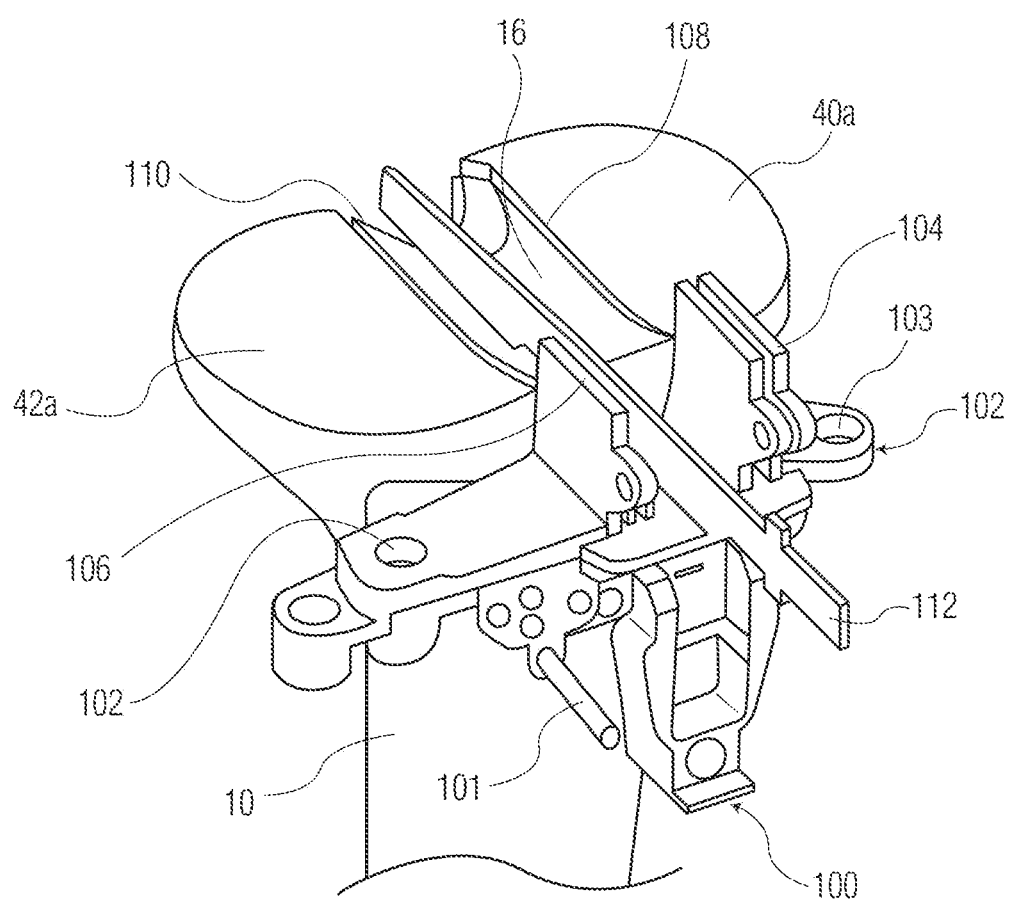
FIG. 7 is an isometric view showing a proximal tibia with a sagittal cutting guide in position to perform the medial and lateral sagittal cuts in the proximal tibia.

The surgical method of preparing the proximal tibia for receiving baseplate 24 will now be described. Referring to FIG. 7, there is shown a standard tibial cutting guide 100, which is typically used to form a proximal resection of the tibia to receive condylar portions 40 and 42 of baseplate 24. Typically, cutting guide 100 is mounted on the anterior surface of the proximal tibia by at least two bone pins 101. Mounted on standard cutting guide 100 is a cutting guide 102 of the present invention adapted to perform a sagittal medial and lateral cut on either side of the tibial eminence 16. The cutting guide 102 is fixedly attached to guide 100 by placing screws or bolts through holes 103 into threaded bores 130 (see FIG. 8) on the proximally facing surface of cutting guide 100. Alternatively, cutting guide 102 may contain dowel pins permanently assembled into holes 103 and releasably attached to cutting guide 100 by engaging dowel pins into precision machined mating bore 130 of cutting guide 100. Guide 102 includes a pair of saw blade guide slots 104, 106 aligned to make lateral and medial resections 108 and 110 in the proximal tibia on either side of eminence 16. As shown in FIG. 7, a saw blade is mounted in slot 106 for making a bone cut which extends distally generally parallel to a sagittal plane through the anatomic axis of the tibia 10. Resections 108, 110 then separate condylar areas of the tibia 40A and 42A from the tibial eminence 16.

Figure 8:
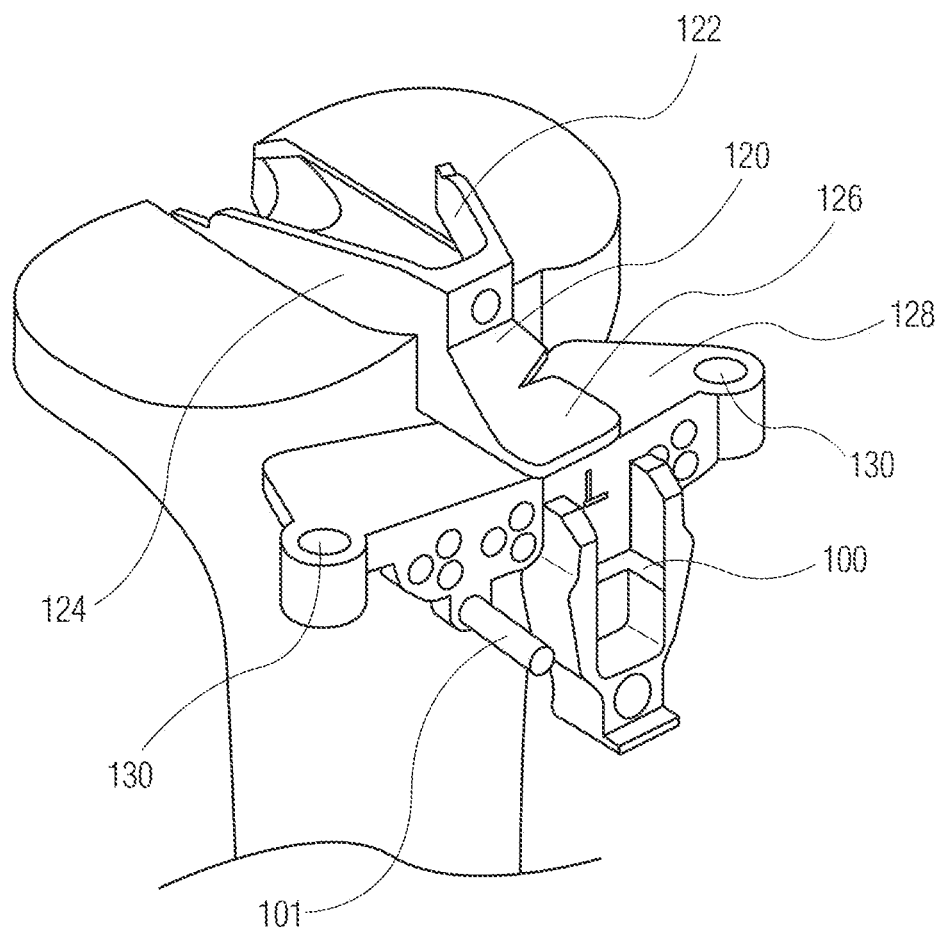
FIG. 8 shows a proximal tibia, including a tibial cutting guide, including an instrument designed to protect the medial eminence located in the previously prepared medial sagittal slot.

Referring to FIG. 8, the proximal tibia is shown with cutting guide 102 removed and a medial eminence protector 120 placed on cutting block 100. Protector 120 has lateral and medial arms 122 and 124, respectively. Arm 124 sits within the previously prepared medial sagittal slot 110. Arm 122 is angled laterally at an angle matching the angle of surface 72 of baseplate 24. To ensure stability, a flange 126 extends anteriorly and sits flush on the saw blade guide proximal surface 128 of cutting block 100. Also seen in FIG. 8 are threaded bores 130 adapted to receive the screws which hold on cutting block 102 shown in FIG. 7.

Figure 9:
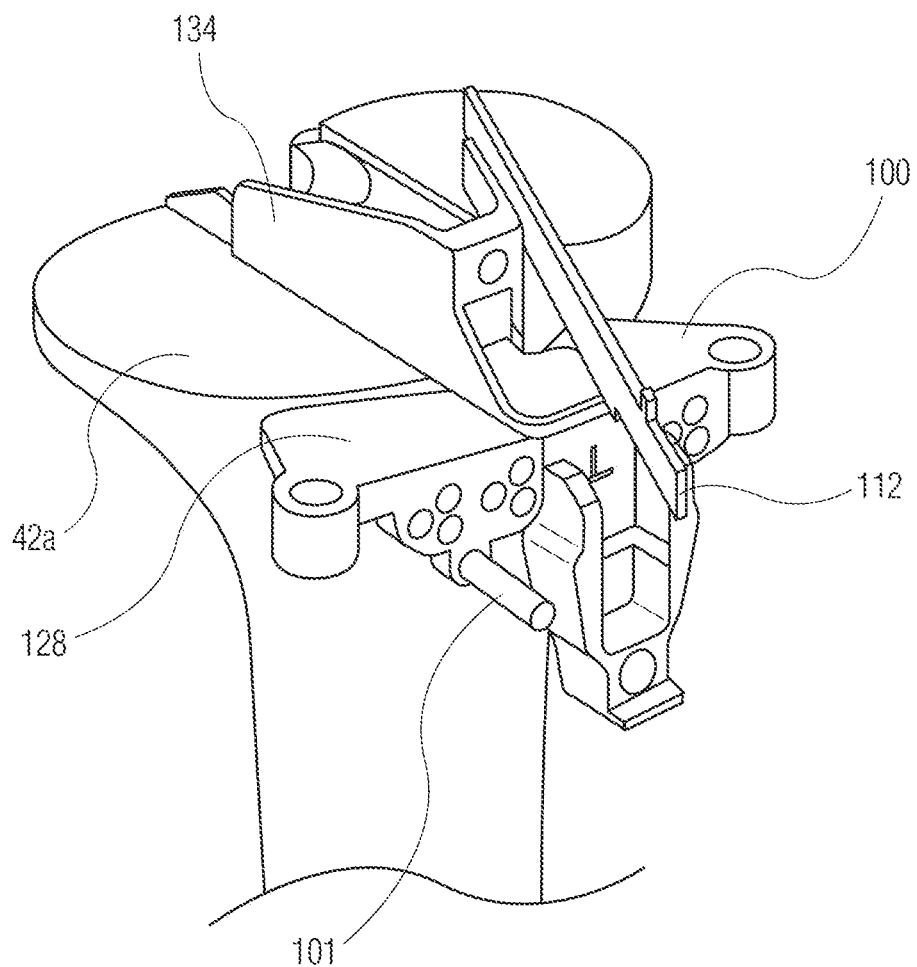
FIG. 9 is an isometric view of the proximal tibia with a cutting guide mounted thereon with a guide surface angled laterally so that a isolatory saw can be used to cut the anterior or lateral corner of the eminence.

Referring to FIG. 9, there is shown saw blade 112 engaging the lateral surface of arm 122 to form the lateral side surface on eminence 16, which engages surface 72 on baseplate 24. By reciprocating blade 112, an oblique cut is made on the anterior-lateral corner of eminence 16. An oscillating saw then can be used on surface 128 to resect the medial tibial condylar portion 42. This leaves a planar surface 42a for receiving the bone contacting surface of condylar portion 42 of baseplate 24.

Figure 10:
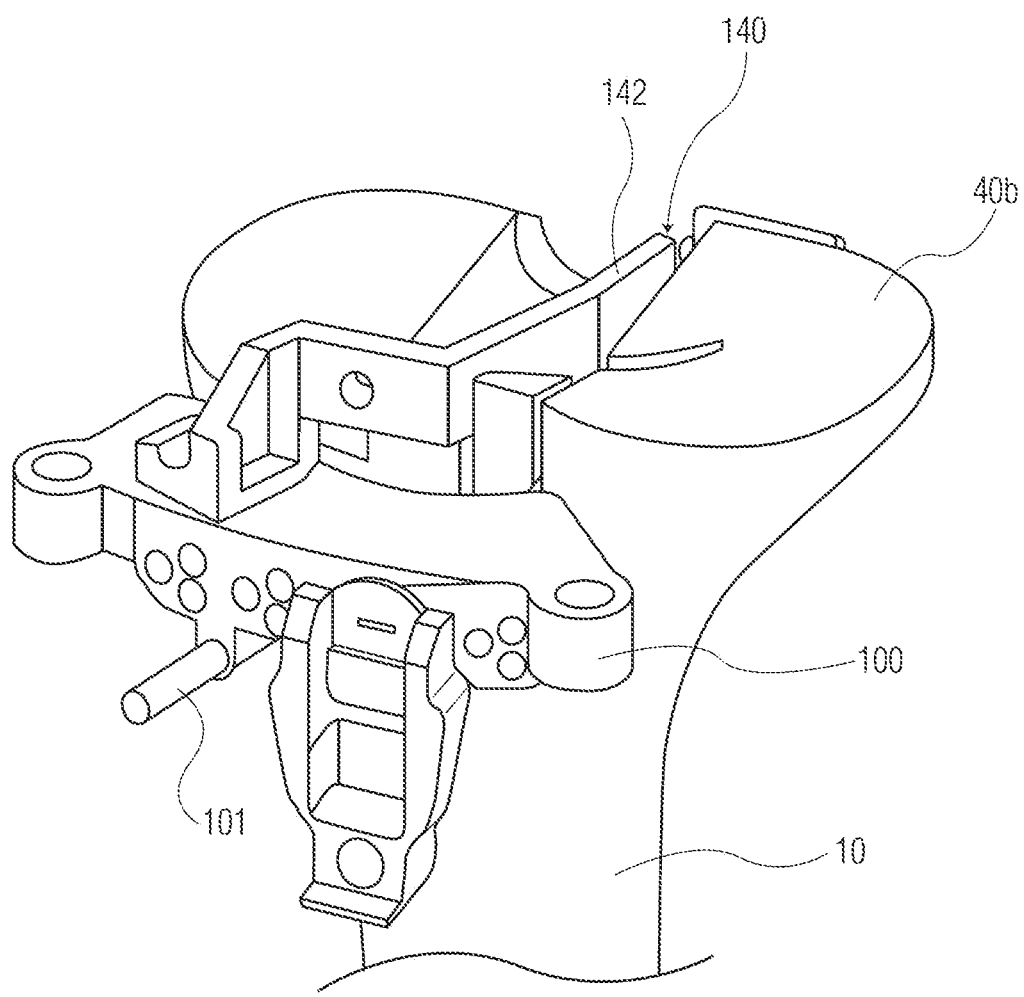
FIG. 10 is an isometric view of a cutting mounted on the proximal tibia and including a lateral eminence protector mounted on the cutting guide.
Figure 11:
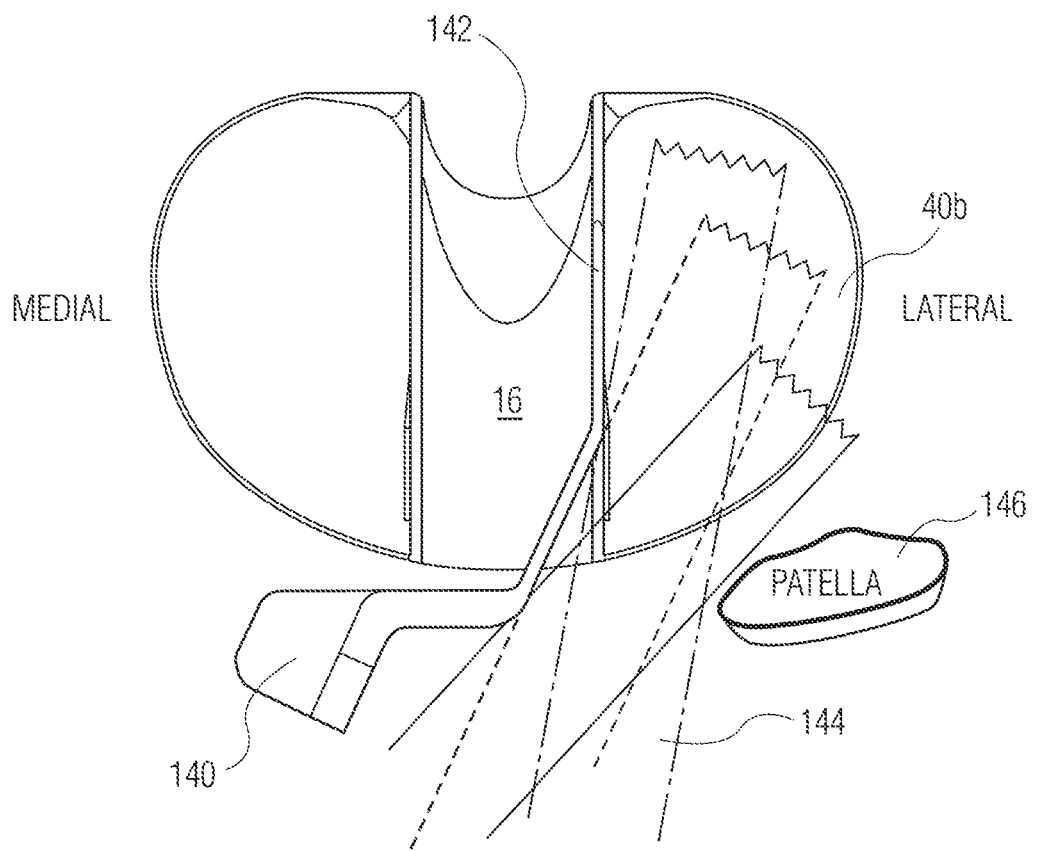
FIG. 11 shows a top view of the instrument end for guiding an oscillating saw blade for resecting the lateral side of the tibia for forming a proximally facing surface thereon.
Figure 12:
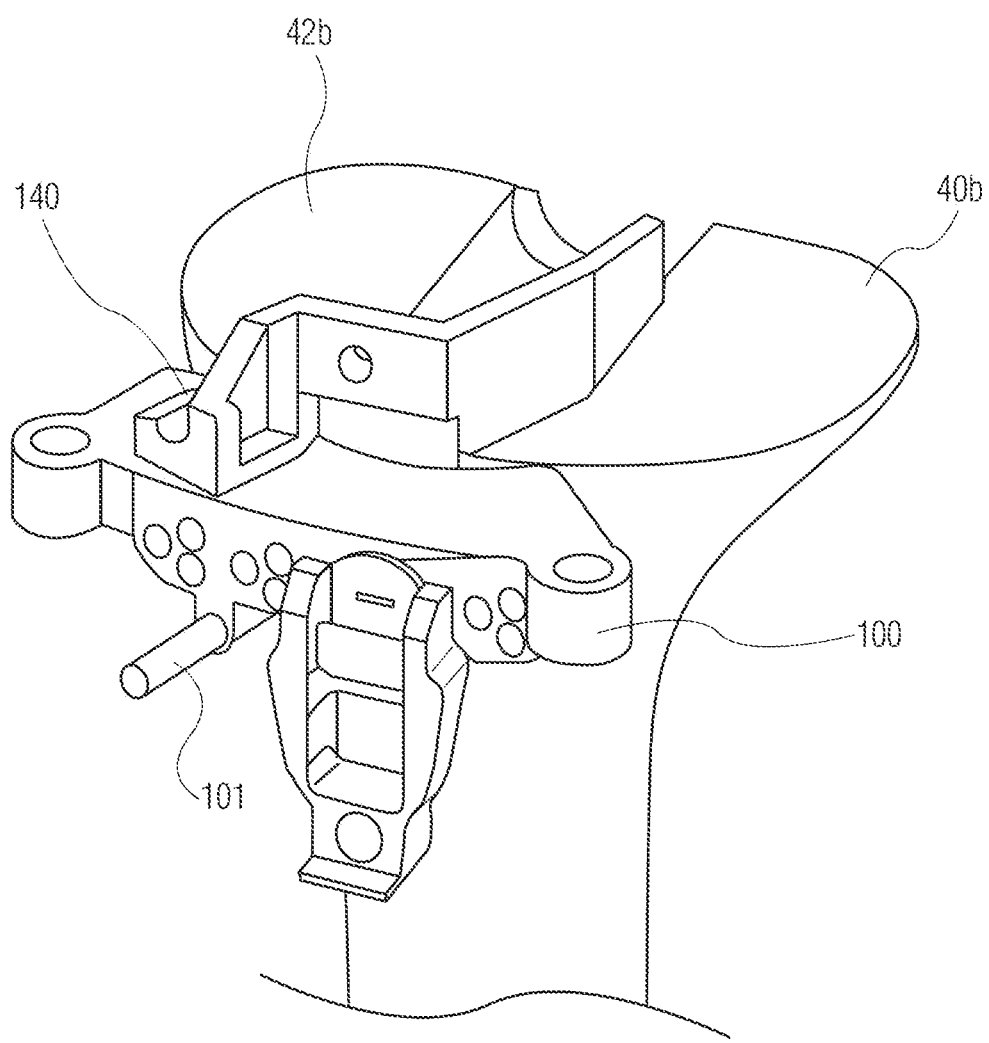
FIG. 12 is an isometric view of the cutting guide of FIG. 11 used to make the shown lateral transverse cut in a manner that protects the eminence.

Referring to FIG. 10, there is shown a lateral eminence protector 140 inserted within the slot formed by saw blade 112 using the lateral angled guide arm 122 of eminence protector 120. Protector 140 allows the resection of the lateral condyle 40b of the proximal tibia using the lateral side of guide 100. Arm 142 prevents inadvertent cutting of eminence 16 during the resection of the lateral condyle. FIG. 11 shows a top view of this resection using an oscillating saw 144. A patella 146 is shown displaced laterally to allow for the resection of the proximal tibia. FIG. 12 shows both the lateral and medial condyles 40b and 42b resected to form a planar proximal surface on the tibia adapted to receive baseplate 24. At this point, cutting guide 100 and protector 140 are removed from the proximal tibia.

Figure 13:
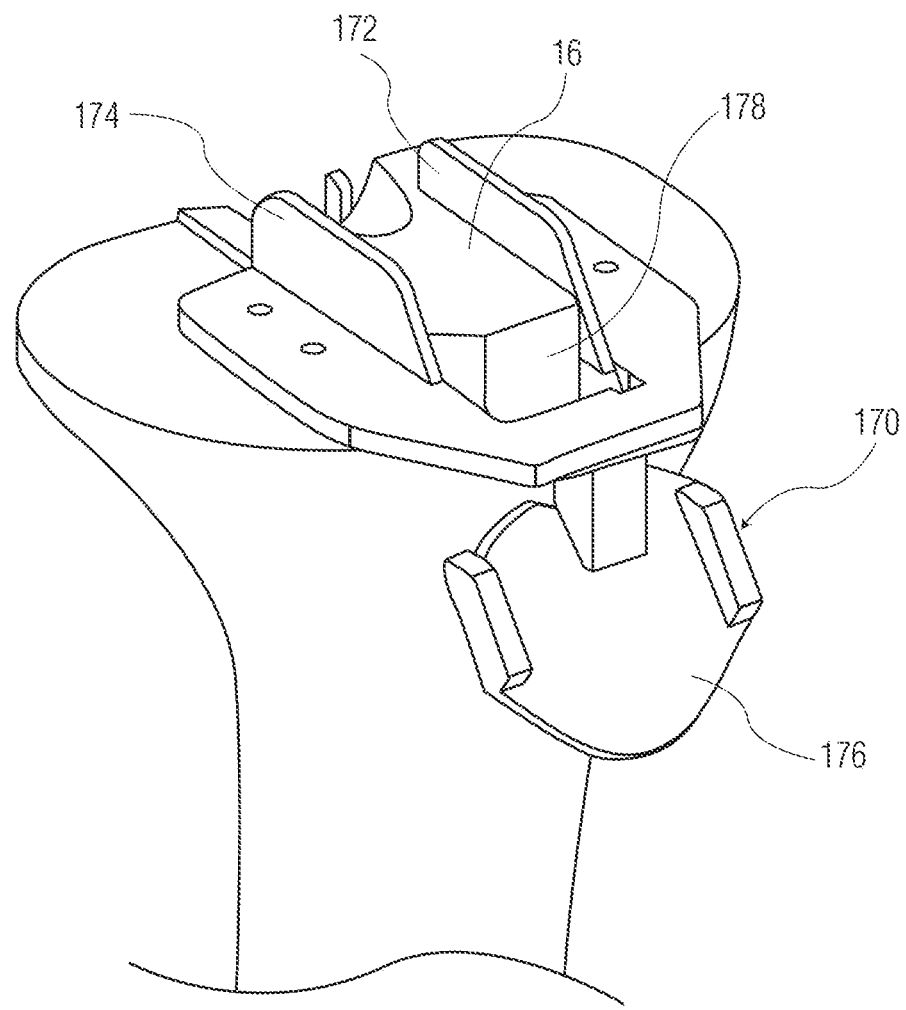
FIG. 13 is an isometric view of an anterior chamfer cutting guide mounted on the resected proximal surfaces of the tibia.
Figure 14:
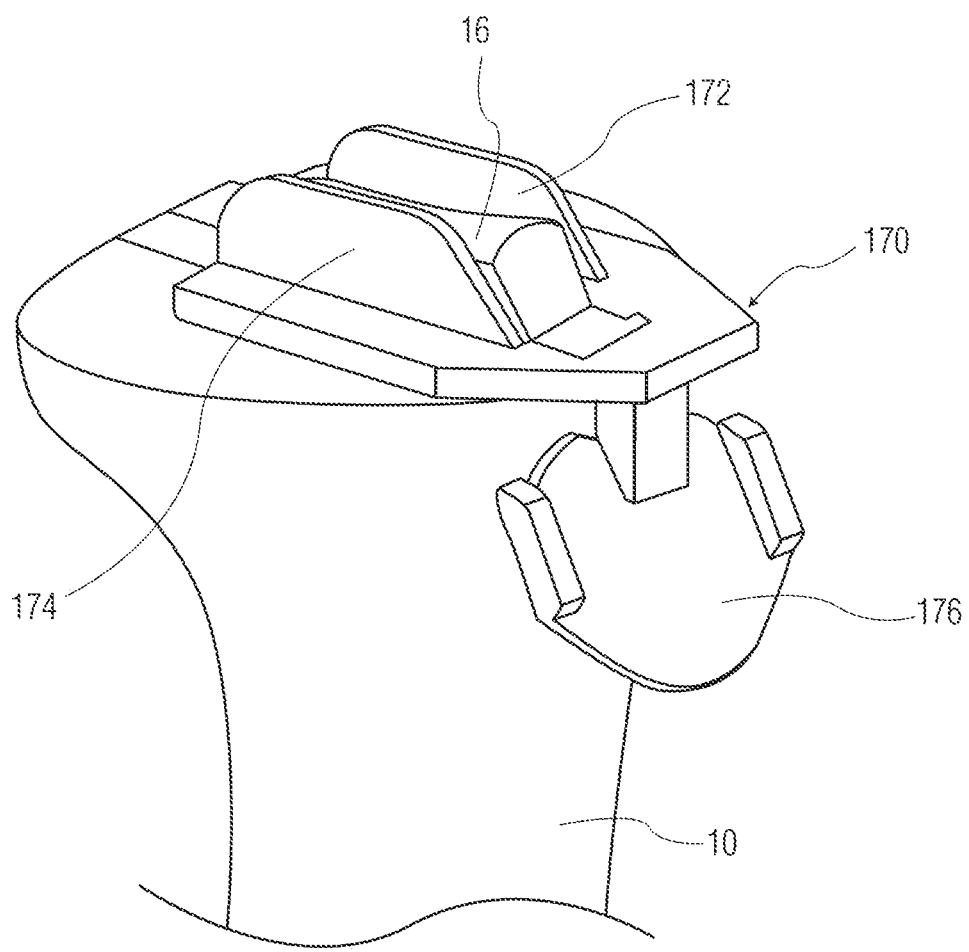
FIG. 14 is an isometric view of the proximal tibia with the anterior chamfer cutting guide mounted thereon after utilizing an oscillating saw to make a resection on the anterior of the eminence.
Figure 15:
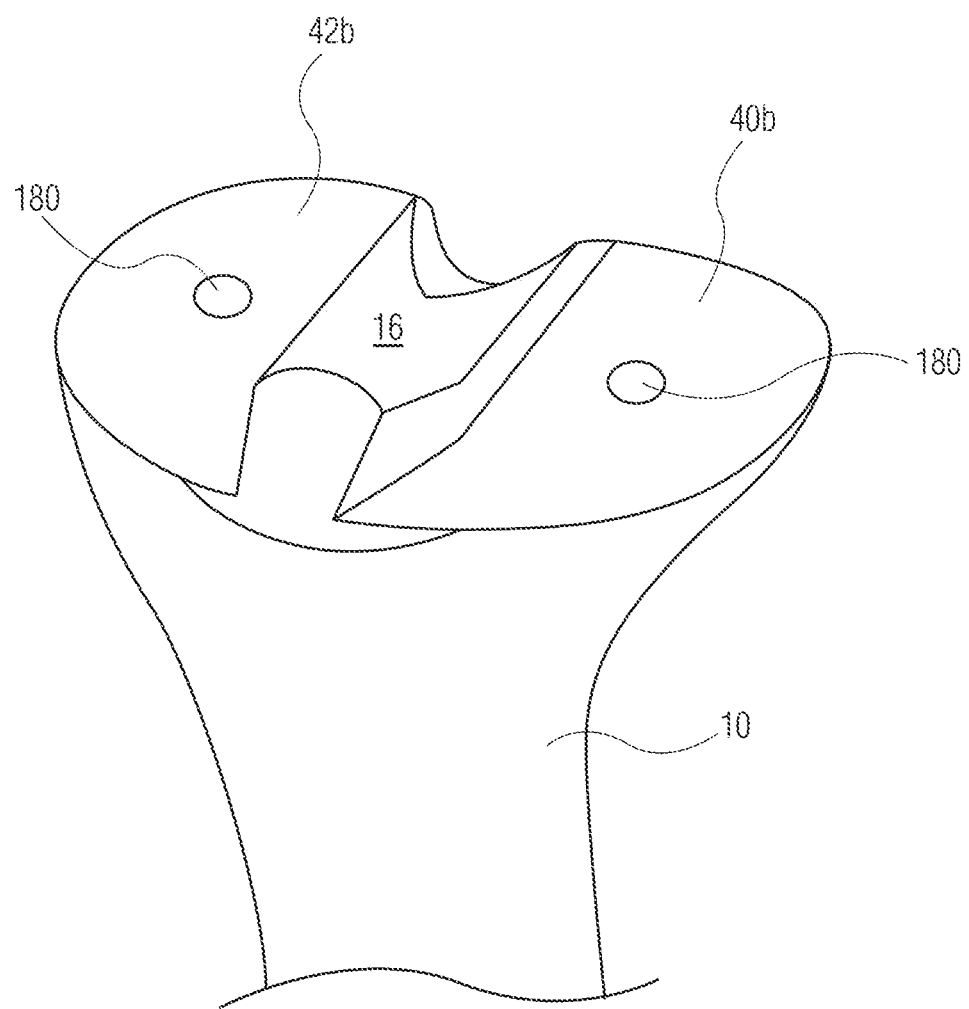
FIG. 15 is an isometric view of the proximal tibia showing the eminence resected in a manner to receive the tibial baseplate of FIGS. 3 and 4.

Referring to FIGS. 13 and 14, with this instrumentation removed, an anterior chamfer cutting guide 170 is placed on the resected medial and lateral planar surface of the proximal tibia. Cutting guide 170 includes arms 172 and 174, which engage the lateral and medial sides of eminence 16, which sides remain after the medial and lateral planar cuts have been made with cutting guide 100. Guide 170 includes an angled cutting guide 176 adapted to guide an oscillating saw blade along a proximal and posterior angled cutting path to resect the anterior edge 178 of eminence 16. This resection is at an angle identical to the angle of angled surface 28 of bridge portion 44 of baseplate 24. FIG. 14 shows the anterior facing surface of the eminence 16 after this final resection has been accomplished. At this point the tibia has been fully prepared as shown in FIG. 15 to receive the baseplate 24. Also shown in FIG. 15 are two angled bores 180 to receive pegs 70. Bores 180 can be made in any standard manner.

Figure 3A:
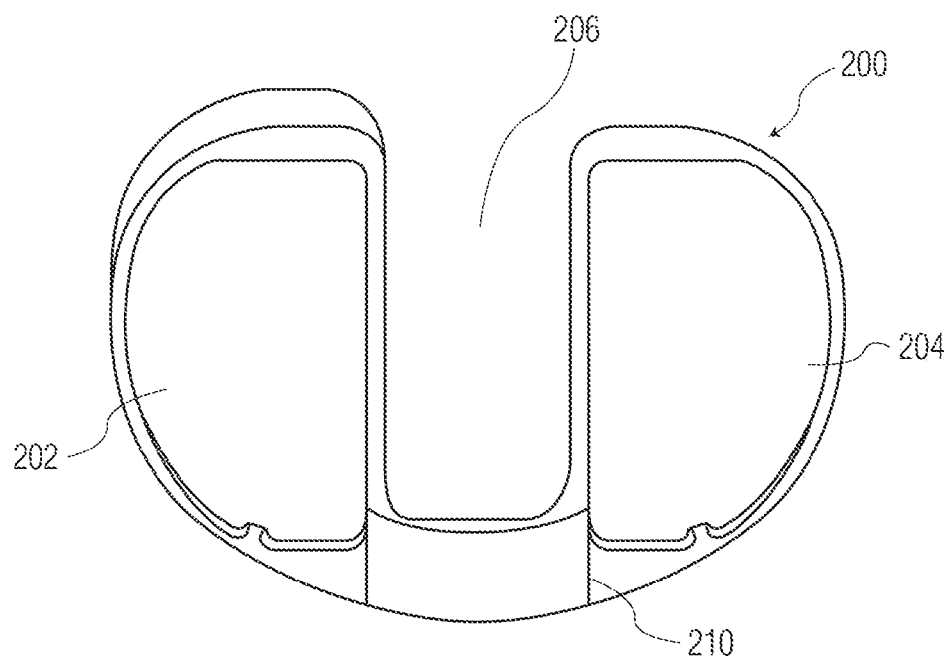
FIG. 3A is a top view of an alternate tibial base plate.
Figure 4A:
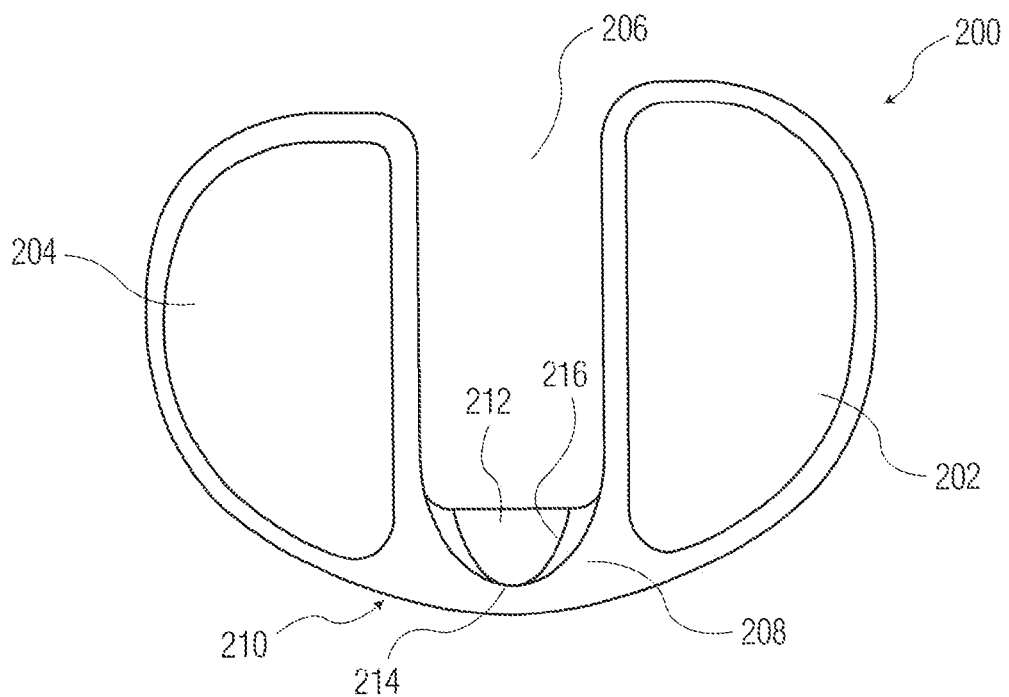
FIG. 4A is a bottom view of the tibial base plate of FIG. 3A having an arcuate anterior recess extending proximally from the bone contacting surface of a tibial base plate.

Referring to FIGS. 3A and 4A, there is shown an alternate tibial base plate generally denoted as 200 which, with the exception of the shape of the distally facing surface in the anterior area, is the same as that shown in FIGS. 3 and 4.

Plate 200 includes medial and lateral condylar portions 202 and 204 respectively. Portions 202 and 204 are again separated by an intercondylar space 206 having a curved anterior portion 208. The outer anteriorly facing surface 210 is identical to that shown in FIGS. 3 and 4.

Posteriorly facing surface 208 at the anterior end of the opening 206 has a planer superior surface 212 which engages the intercondylar eminence compared during surgery. Curved surface 208 tapers posteriorly from its apex 214 posteriorly to a superior curved portion 216. The central cross-section is identical to that shown in FIG. 5.

Figure 16:
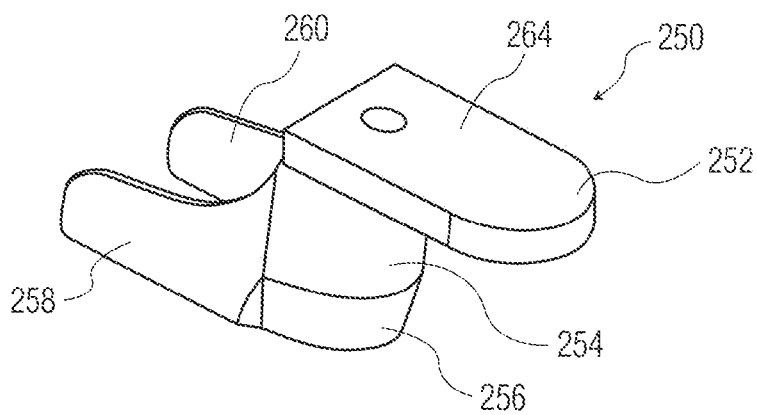
FIG. 16 is a top isometric view of an alternate cutting instrument to be used with the tibial base plate shown in FIGS. 3A and 4A.
Figure 17:
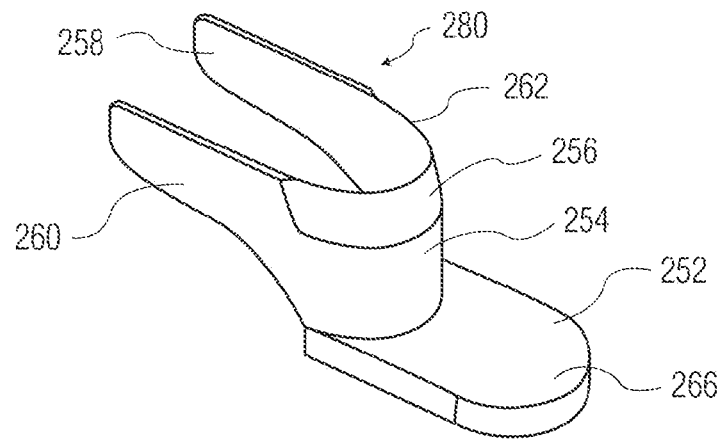
FIG. 17 is a bottom isometric view of the instrument shown in FIG. 16 including various cutting surfaces thereon.

Referring to FIGS. 16 and 17, shows an instrument generally denoted as 250 which is designed to repair the anterior portion of the tibial eminence to receive the tibial implant in FIGS. 3A and 4A. The top view of FIG. 16 shows instrument 250 including a stop flange 252 connected to a curvate portion 254 which has an inwardly tapered portion 256. The instrument includes first and second arms 258 and 260 which straddle the eminence formed as shown in FIG. 7. Thus the instrument 252 takes the place of the instrument shown in FIGS. 8, 9 and 10 which would be utilized when utilizing the base plate of FIGS. 3 and 4.

Referring to FIG. 17 there is shown a bottom view of instrument 250 which includes a sharp cutting edge 262 extending around the circumference of portion 256 and arms 258 and 260.

Figure 18:
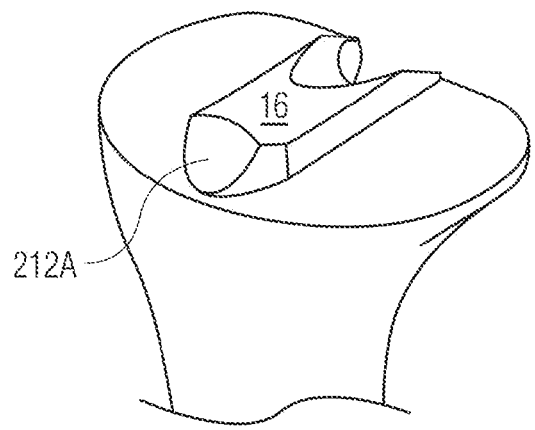
FIG. 18 is an isometric view of the proximal tibia showing an eminence resected to receive the tibial baseplate of FIGS. 3A and 4A.

In use, the instrument 250 is shown in the orientation of FIG. 16 is placed on top of the tibial eminence prepared as shown in FIG. 7. Upper surface 264 of the instrument is then impacted such that cutting edge 262 of arcuate portion 256 is driven distally on the proximal tibia cutting a curved posteriorly tapered surface into the anterior portion of the eminence. Impaction is continued until surface 266, shown in FIG. 17, contacts surface 128 of resection guide 100 thereby forming the curved anterior surface of the tibial eminence 16. The implant of FIGS. 13 and 14 is then attached and the planar cut 212A of FIG. 18 is made. Once this surface is formed the medial/lateral tibial plateaus are resected as shown in FIG. 11.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tibial base component for a tibial implant comprising: a lateral compartment, a medial compartment spaced from the lateral compartment defining an open central section therebetween and a connecting portion connecting the medial and lateral compartments at an anterior end of the base component to be located adjacent an anterior tibia, wherein the open central section of the base component intermediate the spaced medial and lateral compartments is open to a posterior end of the base component, wherein the connecting portion and, the medial and lateral compartments have a bone contacting surface and a superiorly facing surface, the connecting portion having a convexly curved anteriorly facing surface, the convexly curved anteriorly facing surface curved convexly in an anterior direction along an arc lying in a sagittal plane bisecting the open central section of the tibial base component along a proximal to distal extent of the tibial component, and has a first inferiorly facing planar angled surface extending at a first angle from adjacent the anterior end of the base component at a bone contacting surface of the connecting portion proximally and posteriorly to a posterior end of the connecting element, the first planar angled surface defining an anterior end of the open central section at the sagittal plane bisecting the open central section of the tibial base component.

2. The tibial base component set forth in claim 1 further comprising a second angled surface on the tibial component intermediate the medial and lateral tibial compartments extending from a posterior margin of the connecting portion at the bone contacting surface thereof laterally to a medially facing wall of the lateral compartment defining the open central section.

3. The base component as set forth in claim 2 wherein the curve of the anteriorly facing surface of the convexly curved anteriorly facing connecting portion has a radius of curvature centered in a sagittal plane and located posteriorly of the connecting portion.

4. The base component as set forth in claim 3 wherein the connecting portion anteriorly facing surface is curved in a transverse plane.

5. The base component as set forth in claim 2 wherein a planar bone contacting surface surrounds the first angled surface.

6. The base component as set forth in claim 5 wherein the planar bone contacting surface extends laterally at the second angle from a lateral edge of the first angled surface to the medially facing wall of the lateral compartment.

7. The base component as set forth in claim 1 wherein the first angled surface is angled at 20° to 70° to the medial and lateral compartment bone contacting surfaces.

8. The base component as set forth in claim 1 wherein the open central section is defined by parallel medially and laterally facing walls of the lateral and medial compartments respectively.

9. The base component as set forth in claim 6 wherein the connecting portion first angled surface extends between the parallel medially and laterally facing walls.

10. The base component as set forth in claim 8 wherein a second angled surface extends at an angle from an anterior end of the first angled surface at the bone contacting surface laterally to the medially facing wall of the lateral compartment defining the open central section.

11. The base component as set forth in claim 1 wherein the superiorly facing surface of the connecting portion is planar.

12. A tibial base component for a tibial implant comprising:
a lateral compartment, a medial compartment spaced from the lateral compartment defining an open central section therebetween and a connecting portion connecting the medial and lateral compartments at an anterior end of the tibial base component to be located adjacent an anterior tibia, wherein the open central section of the tibial base component intermediate the spaced medial and lateral compartments is open to a posterior end of the tibial base component, wherein the medial compartment, the lateral compartment and the connecting portion have a bone contacting surface and a superiorly facing surface, the connecting portion having a convexly curved anteriorly facing surface, the convexly curved anteriorly facing surface curved convexly in an anterior direction along an arc lying in a sagittal plane bisecting the open central section of the tibial base component along a proximal to distal extent of the tibial base component, and has a posteriorly and inferiorly facing surface extending from a posterior-most point of the inferiorly facing surface of the connecting portion of the tibial base component distally and anteriorly towards an anterior end of the tibial base component, the inferiorly and posteriorly surface defining an anterior end of the open central section at the sagittal plane bisecting the open central section of the tibial base component.

13. A tibial base component for a tibial implant comprising:
a lateral compartment, a medial compartment spaced from the lateral compartment defining an open central section therebetween and a connecting portion connecting the medial and lateral compartments at an anterior end of the tibial base component to be located adjacent an anterior tibia, wherein the open central section of the tibial base component intermediate the spaced medial and lateral compartments is open to a posterior end of the tibial base component, wherein the medial compartment, the lateral compartment and the connecting portion have a bone contacting surface and a superiorly facing surface, the connecting portion having a convexly curved anteriorly facing surface, the convexly curved anteriorly facing surface curved convexly in an anterior direction along an arc lying in a sagittal plane bisecting the open central section of the tibial base component along a proximal to distal extent of the tibial base component, and has a posteriorly and inferiorly facing tapered surface extending from a posterior-most point of the inferiorly facing surface of the connecting portion of the tibial base component distally and anteriorly towards an anterior end of the tibial base component, the inferiorly and posteriorly facing tapered surface defining an anterior end of the open central section at the sagittal plane bisecting the open central section of the tibial base component.

14. The tibial base component set forth in claim 13 further comprising an angled surface on the tibial base component intermediate the medial and lateral tibial compartments extending from a posterior margin of the connecting portion at the bone contacting surface thereof laterally to a medially facing wall of the lateral compartment defining the open central section.

15. The tibial base component as set forth in claim 14 wherein the angled surface extends at an angle from an anterior end of the tapered surface at the bone contacting surface laterally to the medially facing wall of the lateral compartment defining the open central section.

16. The tibial base component as set forth in claim 13 wherein the curve of the anteriorly facing surface of the convexly curved anteriorly facing connecting portion has a radius of curvature centered in the sagittal plane and located posteriorly of the connecting portion.

17. The tibial base component as set forth in claim 16 wherein the connecting portion anteriorly facing surface is curved in a transverse plane.

* * * * *